(12) United States Patent
Schwarz

(10) Patent No.: US 6,542,248 B1
(45) Date of Patent: Apr. 1, 2003

(54) DEVICE AND METHOD FOR THE DETERMINATION OF THE QUALITY OF STRUCTURED SURFACES

(75) Inventor: Peter Schwarz, Geretsried (DE)

(73) Assignee: BYK-Gardner GmbH, Geretsried (DE)

( * ) Notice: Subject to any disclaimer, the term of this patent is extended or adjusted under 35 U.S.C. 154(b) by 0 days.

(21) Appl. No.: 09/517,655

(22) Filed: Mar. 3, 2000

(30) Foreign Application Priority Data

Mar. 4, 1999 (DE) .......................................... 199 09 534

(51) Int. Cl.⁷ .............................................. G01B 11/30
(52) U.S. Cl. ........................ 356/600; 356/446; 356/630
(58) Field of Search ................................. 356/600, 630, 356/631, 632, 445, 446, 448, 237.1, 237.2, 394; 382/108; 348/128; 250/462.1, 463.1

(56) References Cited

U.S. PATENT DOCUMENTS

| 4,613,235 A | * | 9/1986 | Suga ............................ 356/446 |
| 5,141,320 A | * | 8/1992 | Harata et al. ................. 356/630 |
| 5,142,648 A | * | 8/1992 | Fitts et al. |
| 5,401,977 A | * | 3/1995 | Schwarz ....................... 250/559 |
| 5,550,632 A | * | 8/1996 | Harata .......................... 356/446 |
| 5,726,705 A | * | 3/1998 | Imanishi et al. .............. 348/92 |
| 6,266,138 B1 | * | 7/2001 | Keshavmurthy .......... 356/237.2 |

* cited by examiner

Primary Examiner—Hoa Q. Pham
(74) Attorney, Agent, or Firm—Ohlandt, Greeley, Ruggiero & Perle, L.L.P.

(57) ABSTRACT

The present invention relates to a device for a quantified determination of the quality of structured surfaces comprising a first optical device that emits light at a predetermined angle onto the surface to be measured and a second optical device having at least one photo sensor which receives the light reflected by the measurement surface. The optical device are configured such that the reflected light is influenced by the structure of the measurement surface and the reflected light is evaluated by an evaluator, which is provided for controlling the measurement sequence and which comprises a processor and a controller where at least one structural variable is derived therefrom which is characteristic of at least one structural-contingent property of the surface.

78 Claims, 4 Drawing Sheets

DEVICE AND METHOD FOR THE DETERMINATION OF THE QUALITY OF STRUCTURED SURFACES

BACKGROUND OF THE INVENTION

1. Field of the Invention

The present invention relates to a device and method for determining the quality of structured surfaces.

The quality of a surface, or of a structured surface, is to be understood as those physical characteristics which determine the appearance of the surface for a human observer. The characteristics which in particular distinguish a structured surface include structure. color, color brightness, gloss, distinction of image (DOI), haze, surface textures and surface ripples (orange peel), etc.

2. Description of the Related Art

The nature of visible surface properties is an essential constituent of objects in daily life as, for example, all manner of furnishings and consumer objects such as cars, etc.

Within the realm of automobile technology, considerable value is placed on the visual impression created by the visible surfaces. In the following, the technical problems which arise in devising surfaces within the realm of automobile technology will be explained in greater detail without, however, in any way restricting the present invention as regards its scope of application.

Automobile bodies are customarily provided with a high gloss or metallic finish which has far superior reflective or glossy characteristics than the corresponding values of other surfaces such as, for example, furniture. The high gloss to the finish to be applied and the relatively large even surface it will be applied upon necessitate an extraordinarily precise preparation of the surfaces to be finished and an especially high degree of carefulness when applying the finish Various methods, devices and apparatus for determining the visual characteristics and especially the reflective behavior of surfaces are known in the state of the art such as is described in DE 44 34 203 A1.

The automobile industry furthermore also makes use of a plurality of processed structured surfaces in the interior of their cars which are derived from natural materials like, for example, wood or from plastic.

The visual appearance of structured surfaces depends fundamentally on the distinctiveness of the surface structure, although it is also determined by the other afore-mentioned visual parameters.

Automobile manufacturers today employ a large number of inspectors and make use of many high-priced industrial-sized measuring apparatuses to visually or automatically inspect surface quality in order to distinguish surface quality deficiencies while still at the production stage. This method, however, entails a whole set of disadvantages.

The job of a visual inspector is very exhausting and necessitates work bays having precisely defined lighting conditions at all times. Nevertheless, it has still been determined that large discrepancies exist among different inspectors when evaluating the same surface since, for one thing, the respective physiological impressions differ from one inspector to the next and, for another, an individual inspectors' eyesight is also dependant upon his own respective physical constitution.

Thereby, huge difficulties arise in the defining of lower quality thresholds for which a specimen falling short of would be rejected.

Furthermore, it is quite difficult even for experienced inspectors to ascertain the causes of inadequate visual appearance. Especially with regard to structured surfaces, visual appearance is determined by a combination of various parameters so that it becomes difficult, due to the observations and measurements which are carried out, to, for example, modify the control values of an automatic finishing device for the purpose of improving quality.

Structured plastic surfaces are frequently manufactured by means of a stamping procedure in which the molds, embossing rolls respectively, etc., utilized are subjected to abrasive wear-and-tear. With an increasing number of surfaces cast, the structure of the molds employed and consequently also the structure of the plastic surfaces continues to deteriorate. Production quality and quantity can be optimized with a regular replacement of the casting instruments used, although because the lifespan of these tools varies due to fluctuations in their material composition or fluctuations in environmental conditions, they are generally replaced on a regular basis, even before they lose sufficient quality to manufacture finished structured surfaces.

Structured surfaces are increasingly being utilized wherein not only those structured surfaces having a surface structure exhibiting a surface profile in cross section are employed, but also structured surfaces which consistently or in statistical distribution exhibit different visual properties in addition to, respectively instead of, a surface profile.

Such surfaces comprise, for example, a proportion of said surface being of high gloss and another proportion of said surface being of low gloss. Even when these surfaces exhibit no or very little surface profile, an observer will see a distinctive surface structure to said surface. The visual impression on an observer depends upon the relationship between the proportion of the surface which has a high gloss (or respectively has a high reflective proportion) and the proportion of the surface which has a low gloss (or high absorption or scattering respectively). The same applies analogously to the other characteristic visual parameters.

In cases where, for example, the structured surface consists of high gloss sections and low gloss sections, the individual proportional sections can be considered as gloss domains in contrast to the integral gloss relative the entire surface. A characteristic of this is the gloss cover which can be determined as a proportional ratio, respectively difference. Introducing or defining the concept of "gloss domain" allows for a much more unambiguous description of such surfaces in that a gloss parameter can be determined for each respective surface proportion (high gloss, low gloss) which relates to said respective corresponding gloss domain.

Visual testing is very difficult for assessing such surfaces characterized by two, three or multiple gloss effect surfaces since, due to the size of the individual surface elements, the examiner will mainly perceive the overall total impression of the structured surface, making it consequently difficult to render a detailed assessment of the individual surface elements and thus the total surface.

Examples of such multiple gloss effect surfaces include double gloss foils, or also sintered skins having leather or synthetic leather structures.

In addition to the surface's gloss parameter, haze, distinction of image (DOI) and ripples, respectively the individual sections of the surfaces (the "domains"), are also of significance when assessing such structured surfaces.

When automatic devices are used to inspect structured surface quality to determine, for example, surface gloss or distinction of image (DOI), a quantitative numerical scale value can be attained. A decisive disadvantage with visual and also automatic inspections, however, is that although values for the visual characteristics to be tested can be ascertained, the user receives no information as to their basis or cause.

A further disadvantage of conventional measuring apparatuses is that they necessitate considerable space requirements and thereby cannot be portably taken with the user.

BRIEF SUMMARY OF THE INVENTION

It is therefore the task of the present invention to provide a method and a device of the type as identified in the introduction to enable a reproducible assessment of surface quality, and in particular structured surfaces, and that such surface physical variables to be measured can be determined such that a representative characteristic of said surface, contingent upon its structure, can be determined.

Another aspect of the task of the present invention is to provide a device which is smaller and simpler in its construction such that a user can effortlessly take it with him and manipulate it to evaluate a surface without the need to utilize any other aids.

Another aspect of the task of the present invention is to provide a device for measuring visual characteristics which, despite its compact construction in accordance with the previously stated aspects of the task of the invention, provides considerably broadened measurement possibilities in comparison to the known state of the art devices.

A further aspect of the task of the present invention is to indicate a method which enables an advantageous defining of representative characteristics of surfaces as contingent upon their structure.

These tasks are solved in accordance with the present invention as defined in claim 1. The method according to the present invention comprises the subject matter of claim 45.

Further preferred embodiments of the invention comprise the subject matter of the subclaims.

In the device according to the present invention, a first optical means having one or several light sources is provided which directs light at a predetermined angle onto an area of the surface to be measured.

The light reflected by said area of the surface to be measured is received by a second optical means having one or several light-sensitive photo sensors and arranged at a second predetermined angle to said measurement surface.

Said photo sensor or sensors, having at least one, or respectively several, light-sensitive surfaces, emit(s) an electrical measuring signal which is characteristic for the reflected light, whereby said first and second optical means are so disposed that the reflected light will be influenced by the structure of said measurement surface.

Evaluation means are provided in the device according to the present invention for controlling the measuring process sequence and which have at least one processor means and at least one memory means and which evaluate the reflected light, deriving therefrom at least one structural variable representative of at least one of said surface characteristics contingent upon its structure.

Output means arranged in the device according to the present invention serve to relay the measurement values.

The evaluation means utilizes a program stored in the memory means to evaluate the measurement signals and in a preferred embodiment of the present invention, to store said measurement signals and/or measurement values in said memory means.

In another preferred embodiment of the present invention, a plurality of photo sensors are provided in the second optical means and which may be arranged in rows and/or columns.

In contrast to conventional devices, the photo sensors in the device according to the present invention may be arranged on a common substrate. The individual photo sensors may also constitute a linking with light-sensitive surfaces on a common substrate whereby the surface of each light-sensitive sensor is selected or can be selected such that it will correspond to a predetermined reflection angle range within the measurement device.

The device according to the present invention has considerable advantages:

An essential prerequisite for control of the production sequence during manufacture of structured and non-structured surfaces is a determination of the optical quality or the visual appearance of the surface. By means of analyzing light reflected onto the surface, a structural variable is derived which characterizes the surface quality. Conventional visual or automatic measuring methods do not determine a variable for the structure of structured surfaces.

This is particularly advantageous because the structure profile of a structured surface contributes vitally to the overall visual appearance of said surface.

Employing stamping, casting or other such processes results in subjecting the molds being used thereto to abrasive wear-and-tear, its severity dependent upon, among other things, the number of structured surfaces which are produced. In addition to the number of pieces with structured surfaces which are manufactured, other circumstances as well play a decisive role in affecting the quality of the surfaces produced, these factors including environmental conditions such as atmospheric humidity, and air and material temperature.

In conventional manufacturing processes, in order to ensure constant uniform high quality of the manufactured pieces, the molds employed must be replaced after a certain number of stamped or cast pieces have been produced or after a certain amount of time.

This procedure results in an unnecessary high expenditure since, on the one hand, instruments are often replaced which are still of sufficient quality, while on the other hand, it can also happen that due to environmental influences or inhomogeneities and/or variances in the material, instruments will wear out prior to their calculated replacement date.

A regular control system is one possibility for avoiding too much waste. However, in order to examine instruments and tools, the production sequence has to be stopped, which results in costly downtimes.

The device according to the present invention enables a simple, quick and reliable determination of the quality of structured surfaces during the actual ongoing production sequence, so that unacceptable instrument deterioration can be determined in a timely fashion and unnecessary production system downtime can be avoided.

Another advantage in applying the device according to the present invention is that unnecessary frequent replacements of instruments, molds, embossing rolls and other similar equipment employed in the production process does not occur, leading to lower production costs.

Another fundamental advantage of the device according to the present invention is its compact construction; the user can thus portably take it with him at any time.

For this reason, the device according to the present invention is also appropriate for final inspections of hardto-reach spots or in interior areas, such as automobile interiors, where a plurality of structural surfaces are to be found.

A further advantage of such a compactly constructed device is that also the quality of concave or convex curved surfaces can be easily and reliably determined.

Another advantageous consideration is that the device according to the present invention can quickly and easily measure various different sections of a surface to be tested, thereby assessing the distribution of quality and/or reproducibility over the entire surface area.

In a preferred embodiment of one or several previously described configurations of the device according to the present invention which is particularly suitable for application with structured surfaces which have portions or surface elements exhibiting different visual properties, although not restrictively limited thereto, at least one parameter is determined for at least one of the characterizing visual properties of the respective individual types of surface elements.

In a preferred embodiment of the latter described configuration of the inventive device, a variable for the structure of the structured surface is determined from the individual parameters. It is however also possible to determine visual parameters for the individual domains, surface element types respectively, of the structured surface.

The device according to the present invention determines the visual properties or characteristics of individual domains or surface sections of a structured surface.

In a preferred embodiment of the present invention, a coating thickness measuring device is provided for determining the thickness of the coating layer applied to said surface, respectively the coating layers applied to sections of a surface. The coating thickness measuring device comprises one or more coating thickness sensors which generate an electric coating thickness output signal representative of the surface or surface section coating thickness to be determined.

Said control means, which comprises one or more processor means, is provided for controlling the measurement process, and determines one or more coating thickness value(s) by evaluating the coating thickness output signal(s), and determines at least one visual parameter characteristic of said measurement surface by evaluating the light received by the photo sensor(s) as reflected from the measurement surface.

Said output means displays the coating thickness value and said at least one visual parameter relating to a section of the surface, respectively the measurement surface.

An essential prerequisite for controlling the production sequence process when applying finishes to surfaces is the determination of the visual quality of the surface, respectively sections of said surfaces. By means of the above-mentioned visual characteristics, visual parameters may be determined which define the quality of coated and/or structured surfaces. Apart from said visual parameters, the layer thickness of the surface coating (the coating thickness process), respectively the coating layer thicknesses of a structured surface having two or more surface sections, is also an important parameter for the definition of surface quality, and this is not ascertained by conventional visual or automatic measurement methods.

An inventive device according to the present preferred embodiment determines not only one or several visual parameters but also coating thickness, respectively the coating thickness of the individual surface sections, which also represent(s) an essential characteristic of the quality of a coated surface, This is particularly advantageous since coating thickness(es) is/are a very essential parameter when determining surface quality, and because coating layer thickness moreover contains information on the cause of deviations from standard visual parameters.

If an insufficient amount of finish is applied during the coating of a surface, it will not spread properly and inhomogeneities will develop in the coating thickness. If too much finish is applied, it will run, ensuing in surface ripples (orange peel).

When synthesizing and applying the paint, care must be taken in many cases that this process transpires such that the pigments are allowed to float within the applied coating, since the orientation of the pigments relative the coating substrate frequently plays an essential role in color behavior and other visual properties.

This and other causes of deviations in visual properties may be reliably determined by measuring the coating thickness(es).

This is particularly advantageous since the determination of the measurement surface's coating thickness(es) and visual properties yields the parameters most important for determining the defective cause of deviations and thus deriving modified values therefrom for the control of the coating or production equipment.

It is a further advantage of the device according to the present invention that indications of the quality of the surface coating production process itself may be readily and reliably made by correlating visual parameters with layer thickness data derived from measurements made on various points on one coated and structured surface or several coated surfaces.

Tests have shown that the gloss of a surface, for example, correlates to the layer thickness whereas ripples, and hence thickness variation, affects, for example, gloss and haze.

In preferred embodiments of the present invention, the coating thickness measuring device is realized in various ways. In a further preferred inventive configuration, the coating thickness measuring device comprises several different coating thickness sensors.

The coating thickness determination may transpire by means of known devices and methods such as described for example in DE 43 33 419 A1.

For determining the layer thickness on a substrate, usually a coating thickness sensor must be used which is suitable for the particular type of substrate and finish. When measuring layer thickness, a distinction is made between magnetic, nonmagnetic, electrically conductive, nonconductive, non-ferrous or ferrous substrates and coatings.

In a preferred embodiment of the present invention, a permanent magnet and a magnetic flux density sensor means are employed for measuring the layer thickness on a ferrous substrate, whereby in a further preferred embodiment of the present invention said flux density sensor means is configured as a Hall effect sensor means. The magnetic flux density is determined at one pole of the permanent magnet and a coating thickness value is derived therefrom.

For measuring the layer thickness of non-conductive coatings on a conductive substrate, eddy current effects may be utilized.

In a further preferred embodiment of the present invention, a coil induces eddy currents on the surface of the conductive substrate. The resulting eddy currents produce an opposing magnetic field which has an effect on the excited coil, wherefrom a representative value of the coating thickness may be determined. In a preferred embodiment of the present invention said coil is realized as an eddy current measuring coil.

In a further preferred embodiment of the present invention, the coating thickness measuring device comprises an ultrasonic transmitter and an ultrasonic receiver means for the determination of the coated surface layer thickness. The use of ultrasound is especially advantageous for the determination of coating thickness on plastic substrates.

A further preferred embodiment of the present invention provides for a non-contact procedure to determine coating thickness by means of a laser and a thermoacoustical method. It is further possible to determine the coating thickness via acoustical impact upon simultaneous irradiation of the measurement surface with a laser.

In further preferred embodiments of the present invention, a sapphire or hard metal tip is disposed on the gauge probe.

In a further preferred embodiment of the present invention, the coating thickness sensor comprises two coils wound around a ferromagnetic core. The excitation current is carried through the first coil while the signal of the second coil is evaluated for determining the layer thickness. A low-frequency excitation current (<500 Hz) of the first coil allows for measuring thickness of non-ferrous layers on ferrous substrates, whereas high-frequency excitation currents (>500 Hz) allow thickness measurements of non-conductive layers on non-ferrous conductive substrates.

It is further possible to make use of the customary methods and devices known to the expert in an embodiment of the present invention such as, for example, coating thickness measurement processes functioning magnetically or magnetically inductive.

In a further preferred embodiment of the present invention, the coating thickness measuring device comprises at least two different sensor means for determining the layer thickness on the measurement surface. At least one first coating thickness sensor is provided for determining the layer thickness on magnetic substrates, and at least one second coating thickness sensor is provided for determining layer thickness on non-magnetic substrates.

Embodiments of this type have a plurality of advantages. By using various sensor types, the layer thickness or thicknesses on normal and customary types of substrates may be reliably and reproducibly determined.

It is particularly advantageous that the coating thickness measuring device comprises various coating thickness sensors so that the layer thickness of various substrate types may reliably be determined by means of the device according to the present invention.

An embodiment of this type of a device is particularly advantageous because just one single device is all that is necessary to be utilized in order to determine, for example, the coating thickness on various points of a vehicle body or an automobile.

It had previously been necessary to use different devices for different substrates. A further advantage is that, in addition to the coating thickness determination, at least one visual parameter can also be determined.

In preferred embodiments of the present invention, the gloss and/or haze and/or distinction of image (DOI) and/or the typical wavelength and its amplitude determine the coating thickness topology of said measurement surface, respectively the individual measurement surface sections, respectively the types of structured surfaces (orange peel). When determining orange peel, wavelength may ensue at a predetermined wavelength interval or at several wavelength ranges. It is further possible to determine the color(s) of the measurement surface, the individual surface sections of the structured surface respectively, or the color brightness of the respective color.

In a further preferred embodiment, two or more characteristic visual parameters per type of measurement surface are determined. This embodiment is particularly advantageous since by determining two or more visual parameters in combination with the coating thickness, the most essential parameters of said measurement surface(s) are ascertained.

In a preferred embodiment of the present invention, the measuring as or parameters can transpire according to light-field, striae or phase method as described, for example, in "Bergmann Schaefer, "Lehrbuch der Experimentalphysik" {"Experimental Physics Textbook"}, Vol. III, Optics, 8$^{th}$ Edition 1987, Section 3.12, pages 438–452, "although in contrast to the measurement methods described therein, the surface to be tested is not characteristically roentgenized, rather the surface reflection is evaluated. When employing the striae or dark-field methods, the surface is preferably illuminated by parallel light which is reflected and can be focused and said portion thereof can be blocked by a preferably small and/or circular aperture. The reflected light is directed to said aperture which is preferably arranged in the path of the beam, the measuring device respectively. Surface structures and/or aberrations are then essentially mapped on the sensor(s) which can be used for evaluating said surface.

In a preferred embodiment of the present invention, at least a first part of said light irradiated from said first optical means exhibits a light pattern Said first optical means may be provided with a pattern means. In this embodiment of the device according to the present invention, the light emitted from said at least one light source of said first optical means is at least partially irradiated at said pattern means The amplitude and/or phase of the light transmitted through said pattern means becomes influenced by the corresponding pattern of said pattern means.

In another preferred embodiment of the present invention, the light pattern irradiated from said pattern means has at least one light/dark edge, or a plurality of light/dark edges, whereby in a further embodiment of the present invention, at least a part of said plurality of light/dark edges is dispersed at least sectionally parallel to one another.

Said pattern of said pattern means may be arranged symmetrically to the optical axis. In the event that the irradiated light pattern has a plurality of light/dark edges, the individual light/dark edges may exhibit a straight, circular or sinusoidal shape.

In a preferred embodiment, at least a portion of said plurality of light/dark edges exhibits grid, lattice or circular form.

The projection of a light pattern onto a surface to be tested is especially advantageous since an evaluation of the light pattern reflected from said inspected surface, measurement area respectively, enables conclusions to be drawn about the quality and the structure of the measurement surface to be tested.

It is possible that said light pattern will not exhibit a sharp transition from light to dark, but rather the intensity of the projected light will be somewhat influenced into a sinusoidal or saw-toothed shape.

In a further preferred embodiment of the present invention, a first part of said light transmitted from said first optical means is directed onto the measurement area with said light pattern, while a second part is directed onto said area without the light pattern However, the pattern means of the device according to the present invention may also be made variable such that alternating measurements, meaning including light pattern and omitting light pattern, are also possible.

This makes it possible for said pattern means to be provided with, for example, an LCD device for linking individual sections or individual pixels to various different light patterns as desired, thus allowing the light pattern to be adjusted and/or switched off quickly and easily according to the given requirements.

By evaluating the signal of said at least one photo sensor, which receives at least a portion of the reflected light pattern, said evaluation means can determine a structural variable which is representative of at least one characteristic of said surface contingent upon its structure.

In a further preferred embodiment of the present invention, said evaluation means determines a gradation of the electrical and/or digital measurement signals for at least one portion of said plurality of photo sensors from the difference defined between said photo sensors' electrical and/or digital measurement signal and the electrical and/or digital measurement signal of the next photo sensor in the row and/or column, or in the difference between said photo sensors' electrical and/or digital measurement signal and the electric and/or digital measurement signal of at least a portion of the directly or diagonally adjacent photo sensor.

This is especially advantageous because the gradients of the measurement signals, and the gradients of the measurement signals upon irradiation with a light pattern in particular, are well-suited to derive a structural variable representative of at least one structurally-contingent characteristic of the measurement surface to be tested.

In a further preferred embodiment of the present invention, said evaluation means determines at least one average from at least one portion of said photo sensors' measurement signal gradient and from this determines at least one average of said characteristic structural variable for said at least one structurally-contingent characteristic of said surface.

In addition, a histogram may also be determined from these gradations, in which a range of predetermined or variable gradients exceeding said gradations can be plotted in the corresponding intervals, respectively ranges. By the formation of this gradient center focus and/or mean value, said evaluation means can derive a characteristic structural variable which is representative of the structurally-contingent characteristics of said surface.

This preferred embodiment of the present invention is particularly advantageous because through the determination of at least a portion of the gradations and through the definition of an average gradient, a characteristic structural variable for the measurement surface can be determined quickly and reliably.

Blunt or rounded-off surface structures resulting from, for example, when old or worn out tools are utilized during production of structured surfaces, reflect light projected thereupon more diffusely than surfaces with a more sharper distinct profile.

It is therefore possible to determine the structurally-contingent characteristics by means of the utilization of such an embodiment of the device of the present invention.

In another preferred embodiment of the device in accordance with the present invention, at least one, two, three or more characteristic visual parameters of said measurement surface are determined in addition to said characteristic structural variables.

In a preferred embodiment of the invention, the gloss or haze or distinction of image (DOI) or a representative measure of typical wavelength and amplitude (orange peel) of the measurement surface coating topology is determined.

Orange peel determination transpires at a predetermined wavelength interval, evaluating the determination of orange peel, however, may also transpire under two or more different ranges of wavelength. Furthermore, it is also possible to determine the measurement surface's color or color brightness.

In a preferred embodiment of one or several of the previously described configurations of the present invention, the inventive device detects a curvature of the surface and preferably determines same numerically. Preferably, a mathematical compensation of the measurement can transpire according to said determination of the (local) curvature.

In the present embodiment, a light pattern is preferably projected onto the surface to be tested according to one of the previously described configurations and embodiments.

Should the surface to be measured exhibit a curvature (convex or concave), its edges will be enlarged or reduced upon illumination with, for example, a saw-tooth pattern. Upon illumination with a (grid, lattice) pattern, the curvature can be determined by, for example, determining the spacing between the individual lines. As soon as the curvature is determined, the corresponding values for correcting or compensating of the visual measurement values as returned by the measuring device can be applied, so that the end result, i.e. measurement values subsequent to compensation, are then essentially unaffected by the surface curvature.

In a further preferred embodiment of one or several of the previously described embodiments, the sharpness of depth as optically mapped can be objectively influenced, reduced or enlarged to compensate for a curvature of the surface to be measured.

In a further embodiment of the present invention, the sharpness of depth is decreased in curved surfaces. A mapping of the measurement surface is thus blurred and the measurement results are no longer or only negligibly influenced by the curvature.

In a further preferred embodiment of the present invention, a surface curvature is determined automatically and likewise automatically compensated.

In a preferred embodiment of one or several of the previously described configurations of the present invention, at least one, two, three or more characteristic visual parameters are determined for each surface element type on the structured surface. Preferably the gloss and/or the haze and/or the distinction of image and/or the orange peel of the individual surface element types are determined.

Along with the parameters for the individual domains, for example the parameters for the gloss domains, a variable for the structured surface is also preferably determined which defines the quality of said structured surface. This preferred embodiment is particularly advantageous in cases where the structured surface has at least two surface element types which differ in their characteristics, preferably visual characteristics. It is moreover possible to determine the total coverage of the individual visual parameters relative the measurement surface.

In another preferred embodiment of the present invention, in addition to said structural variable, even more of the above-cited characteristic visual parameters are determined.

Such an embodiment of the inventive device is especially advantageous since, among other things, all vital and contributive visual and physical characteristics of said measurement surface can be determined by employing this compact device.

In an advantageous configuration of all of the previously described embodiments, a third optical means is arranged comprised of at least one light source irradiating light having a predetermined spectral characteristic and directed onto the measurement surface at a predetermined angle.

In the previously cited preferred embodiments of the device according to the present invention, the predetermined angle at which the light is emitted from the first optical means to the measurement surface, and/or the predetermined angle at which the second optical means receives the light reflected from said measurement surface, and/or the predetermined angle at which the light emitted from the third optical means is directed onto said measurement surface, may be optionally adjusted as individually desired, and includes in particular angles of 5°, 10°, 20°, 30°, 45°60°, 75°, 80°, and 85° from the norm between the measurement surface and the corresponding angle of light. It should be accentuated, however, that other angles in addition to those cited here are also possible.

In such an embodiment, preferably at least one of said optical means is of variable position. Preferably said positional change may transpire automatically upon changing of the angle(s) and a rotation can take place about the measurement point. A synchronous or simultaneous movement of several optical means is then also possible so that the angle of incidence, emergent angle respectively, remains the same. It is however also possible that at least one optical means may be movable essentially perpendicular to the surface to be measured. In this configuration, preferably at least the first and the second optical means may be movable perpendicular to the surface to be measured so that the light emitted by said first optical means and reflected by the surface may be received by said second optical means.

In a further preferred embodiment of the present invention, said light irradiated from said third optical means is directed at such an angle onto the surface that the light directly reflected from said measurement surface according to a Fresnel reflection has a different angle with respect to said measurement surface than the angle between said measurement surface and said surface reflected light which is emitted from said first optical means, so that said second optical means, the photo sensors respectively, in essence receive light irradiated from said third optical means and diffusely reflected by said measurement surface.

Said at least one light source of said third optical means may have one, two and—especially preferable—three light-emitting elements with each light emitted having a different spectral characteristic so that a varied range of emitted wavelength results.

The emitted wavelength ranges of said light-emitting elements may at least partially overlap with respect to their spectral characteristics in the range of the visible light spectrum, and in a further preferred embodiment of the device according to the present invention, the emitted spectral characteristics of said light-emitting elements are linearly independent from one another.

In a further preferred embodiment of the present invention, at least two, preferably three or more, photo sensors, respectively photo-sensitive elements are disposed in such a manner as to differ with respect to their spectral characteristics so that the ascertained color of the reflected light will serve as a visual parameter of said measurement surface.

In another preferred embodiment of the present invention, at least one photo sensor is provided with at least two, preferably three or more, photo-sensitive elements having electrical outgoing signals which can be individually determined and which differ with respect to their spectral characteristics so that the color of light reflected from said measurement surface can be ascertained.

An embodiment of the device according to the present invention which enables ascertaining the color of the light reflected from the measurement surface is of particular advantage since color and color brightness are essential characteristic features of both surfaces as well as structured surfaces.

In a further preferred embodiment of the device according to the present invention, one or more light-emitting diodes or laser light sources are arranged in said first and/or said third optical means.

At least a portion of said essentially direct or diffuse light emitted from said first optical means and/or said third optical means is preferably essentially parallel, divergent or convergent.

In a preferred embodiment of the device according to the present invention, the light emitted from said first and/or third optical means is convergent light directed onto the surface to be measured and is then preferably focussed such onto the surface to be measured that it only illuminates an area within the proximity of one measurement point, respectively one spatially small measurement surface on the surface to be measured.

In a preferred embodiment of the latter described configuration, a scanning means is preferably provided in the first optical means which consecutively scans an illuminated light spot section of the surface to be tested at a ratio (>5, preferably more than 10, preferably >50) to said surface. Said embodiment may also utilize a point focussing of the ray(s) of light directed onto the surface to be tested as well as illumination employing a spatially extended light spot.

In another preferred embodiment of the device according to the present invention, said first and/or third optical means emits at least one point of light with a predetermined diameter perpendicular to the propagated extension of said irradiated light or at least one strip of light with a predetermined length and width perpendicular to the propagated direction of said irradiated light.

The light pattern projected by said first optical means may also be comprised of different points or strips of light.

It should be pointed out that said at least one visual parameter, said structural variable respectively, may also be determined from said photo sensors' electrical and/or digital measurement signals, which receive said second part with omitted light pattern of said light irradiated from said first optical means as reflected from said measurement surface.

In a further preferred embodiment of the device according to the present invention, at least one temperature measuring apparatus is arranged in as close proximity as possible to said at feast one light source of said first optical means and/or said at least one light source, at least one light-emitting element respectively, of said third optical means and/or said at least one photo sensor, said at least one photosensitive element respectively, with which a determination of the characteristic temperature of the respective light source, light-irradiating element, photo sensor or light-sensitive element can be made, so that a temperature-corrected determination of said at least one structural characteristic value and/or said at least one visual parameter can be made.

The determination of characteristic temperatures of the light sources and photo sensors is especially advantageous since functioning of these electrical devices is dependent upon temperature, and measurement reproducibility will increase with a temperature-corrected determination of parameters and characteristic values by virtue of the fact that the temperature and its distribution within the device in accordance with the present invention can change with increasing elapsed measurement times or with changing of measurement apparatuses.

In another preferred embodiment of the present invention, at least a portion of the path of said plurality of photo sensors' mapped light pattern is determined. A characteristic profile height parameter of said measured surface can be determined from the course deviation of the measured path from the ideal path.

In an especially preferred embodiment, the path of at least one light/dark edge is determined in sections on said plurality of photo sensors or on a CCD chip respectively.

Should a light or dark line be projected onto a measurement surface exhibiting a rectangular profile with a profile height h, a spatial separation of said line reflex then occurs on the CCD chip of said second optical means.

The portion of dark or light lines reflected from the lower edge of the rectangular profile are spatially displaced parallel to those reflected at the upper edge of the reflected rectangular profile.

The reflected image of an ideal rectangular structured surface is two dotted light or dark lines on the CCD chip.

With the known emitted and reflected angles and the spacing between said two dotted lines on the CCD chip, the profile height can be determined at every point on the measurement surface.

When measuring non-rectangular surface profiles, a profile height characteristic value of such measurement surfaces can be determined analogously by utilizing the corresponding geometrical relationships.

The determination of a profile height characteristic value is particularly advantageous since the profile height of the pieces fabricated can also decrease when manufacturing tools wear out.

In another preferred embodiment of the present invention, the structural variable is determined by means of a triangulation process, whereby this determination of said structural variable may ensue solely or also additionally by means of said triangulation process. It should be pointed out that any one of the common triangulation procedures as have become known in the state of the art may be used.

Exemplary hereto are the triangulation procedures described in the U.S. Pat. Nos. 5,546,189 and 5,744,793, which hereby become a part of the disclosure of the present invention.

In a further preferred embodiment of the device according to the present invention, in contrast to the procedure as described in U.S. Pat. No. 5,546,189, there is no gray value, or not just a gray value solely which is then determined to be deemed representative for the measurement surface height at the measured location. Rather, the measured location's surface height is determined with the utmost precision.

In a further preferred embodiment of the invention, an additional optical means with at least one photo sensor is provided which is directed to said measurement surface at a predetermined angle. In a particularly preferred embodiment, this additional optical means is arranged in the plane extending between the point of measurement, the second optical means and the third optical means. Especially preferred is that the angle at which said additional optical means receives reflected light is the same as the angle at which the second optical means receives reflected light, so that the second and the additional optical means are arranged symmetrically to the light emitted from the first optical means or to the light emitted from the third optical means.

In a further preferred embodiment of the invention, the intensity and the point at which the reflected intensity impinges said second optical means and said additional optical means is determined; particularly preferred is saving a characteristic site evaluation value for the point measured and the measured intensity in the memory means, and that said evaluation value defines a characteristic clearance parameter value for the spaced distance to the point of measurement on the surface to be tested and saves same in said memory means.

In a further preferred embodiment of the invention, a scanning device is provided in the first optical means which scans the surface to be tested in such a manner that the light irradiated by said first optical means is scanned chronologically.

Of particular preference is that said evaluation means determines at least one of said at least one structural variable from its evaluation of said clearance parameter and said measured point characteristic values.

In another preferred embodiment of the device according to the present invention, at least one quantitative slope gradient parameter is determined for the slope characteristic of the structure of the surface to be measured.

In a further preferred embodiment of the present invention, said evaluation means determines at least one quantitative focus parameter for the definition of sharpness of the edges of the surface to be measured.

These embodiments are especially advantageous because as tools and instruments wear out, the structure of the surface of the pieces manufactured degrades; structure slope gradient in particular decreases through tool wear and tear, as does the definition of focus of the edges, because increasing wear and tear causes a rounding off or blunting of the tool profile.

In a further preferred embodiment, an evaluation structural variable is derived from said at least one structural variable and at least one of the afore-mentioned characteristic visual properties (gloss, haze, DOI, orange peel) which is characteristic for at least a portion of the visual characteristics of the surface.

In evaluating surfaces, and especially structural surfaces, their visual appearance does not depend solely on their structure distinction, but rather also on the other characteristic visual properties cited. For example, with especially smooth and highly reflective surfaces, the demands placed upon the manufacturing process are exceptionally high, since on such surfaces the human eye perceives even the smallest of blemishes, unevenness and variations. With automobiles having a so-called "metallic" finish, it is virtually impossible to rectify defects in the finish over a large surface in such a way that these defects will be invisible to an observer.

In contrast thereto, the demands placed upon the coating quality of finishes for matted and less reflective surfaces and the surfaces underneath them are considerably less.

While even small measures of surface roughness and orange peel do disturb the physiological feeling of an observer when regarding high gloss surfaces, far larger instances of surface roughness and ripples in less reflective and matted surfaces have only little or no disturbing effect on the visual impression of an observer. With structured surfaces, visual impressions which are contingent upon its structure are less dependent on surface roughness, gloss or the other visual parameters.

Therefore, in accordance with this preferred embodiment of the present invention, at least one evaluation structural variable and at least one of the cited characteristic parameters, representing a measure of the quality of the measured surface, are defined.

According to another preferred embodiment of the present invention, at least one evaluation structural variable is likewise defined. Especially, but not only with structured surfaces which have only a small or no surface profile, and the at least two surface element types which differ in at least one of their characteristic visual parameters, said evaluation structural variable is at least defined by one of the designated characteristic parameters. With such structured surfaces, the visual impression and the quality of distribution uniformity is dependent upon the visual parameters.

In a preferred embodiment of the present invention, an evaluation structural variable is defined from said measurement surface gloss characteristic value and said structural variable so that a sufficient and/or satisfactory evaluation structural variable can be defined for low-gloss surfaces even when they exhibit a less than ideal structural variable.

In a further preferred embodiment, said evaluation structural variable is defined in such a manner that, for example, a higher gloss will counterbalance a poorer structural variable, so that said evaluation structural variable achieves a qualitatively satisfactory result.

In a further preferred embodiment, an evaluation structural variable is defined for at least two or all of the cited visual values (gloss, haze, DOI, orange peel) or that an evaluation structural variable is derived from two or more of the cited characteristic values (gloss, haze, DOI, orange peel) together with said structural variable, said evaluation structural variable being characteristic of the visual appearance of the measured surface.

The derivation of at least one evaluation structural variable from said at least one structural variable and at least one of said characteristic visual values such as gloss, for example, is especially advantageous, since it enables an especially easy and automatic or automated determination of the quality of the surface to be tested.

In another preferred embodiment of the device according to the present invention, at least one lower or upper threshold value is definable for said at least one structural variable and/or said at least one characteristic visual parameter and/or said at least one evaluation structural variable, and which upon this defined threshold being either undercut or exceeded, a message is sent to the output device or an audio or visual alarm signal issues.

In another preferred embodiment of the present invention, said at least one threshold value is automatically determined through measurement of at least one reference surface For example, A is possible that one, two or more evaluated reference surfaces of differing qualities are measured, whereby advantageously at least one of said reference surfaces is of higher quality and at least one other is of inadequate quality.

Such a semi-automated calibration of said device allows for a quick and reliable measuring of various measurement points on one surface or on various different surfaces to be tested.

In a preferred embodiment of the device according to the present invention, such a semi-automated calibration is performed by measuring of at least one reference surface for each surface element type comprising said structured surface.

A further preferred embodiment provides a circuit breaker, ON-OFF switch respectively.

Furthermore, an input means can be provided on the device according to the present invention for the purpose of, among other things, enabling the user to input a type designation for the type of surface to be measured, whereby said evaluation means evaluates subsequent measurements with reference to this type designation and then files same in said memory means.

In another preferred embodiment of the present invention, upon switching-the device on, an audio or visual signal prompts the user to enter a type designation into said input means for the surface type to be measured, whereby in an especially preferred embodiment, the user can change the surface type at any time by entering in another type designation to which all subsequent measurements will make reference.

The input and/or choice of type designation prior to the measurement of a particular surface type is especially advantageous because in evaluating various different types of surfaces, the individual characteristic values are of differing significance and they convey differing degrees of importance in the forming of an evaluation structural variable.

In a further preferred embodiment of the present invention, the user can indicate his own evaluations of each measurement of a particular surface according to his own physiological impressions through the input of a user-defined assessment value in said input means. Particularly preferred is the long-term filing in said memory means of said user-defined assessment value together with said at least one characteristic visual property and said at least one structural variable and said at least one evaluation structural variable. Hereby, the range of said user-defined assessment values has to encompass at least two differing values of quality corresponding to "good" and "poor."

In another preferred embodiment of the present invention, at least a portion of said user-defined assessment values together with the relevant corresponding measurement parameters and characteristic values filed in said memory means is used for the automatic determination of at least one of said at least one threshold value for the particular type designation of the surface to be tested.

In another preferred embodiment of the device according to the present invention, said evaluation means takes into account essentially all of the user-defined assessment values and the corresponding parameters and characteristic values and structural parameters for the determination of said at least one threshold value and for the determination of the factors of significance, which are utilized in the determination of the evaluation structural variable, as stored in the memory means relevant to the type designation for a particular surface to be measured, so that with an increasing number of measurements made, said factors of significance and said at least one threshold value adjust in order to adapt said evaluation structural variable to the user's visual impressions.

This preferred embodiment of the present invention is particularly advantageous since the device is "intelligent;" it is adaptive when determining said parameters and characteristic values and said evaluation structural variables and thereby the application of such an intelligent system continually increases the reliability and efficiency in determining said at least one evaluation structural variable as the number of measurements carried out increases.

It is furthermore to be noted with this preferred embodiment that in the determining of said threshold values and factors of significance, not all measured and stored values for said type designation are utilized, since a user's physiological condition has an effect on the evaluation of said measurement surface, and since a determination of undesirable thresholds and/or factors of significance may result from errant input of incorrect user-defined assessment values.

For example, it is possible that given a plurality of available measurement results, a particular percentage, for example 5% or 10%, will not be considered during the determination of said factors of significance and said threshold values, whereby selection of the values not to be considered transpires in accordance with known statistical techniques.

This embodiment of the present invention is particularly advantageous as neither does it consider errant input of incorrect user-defined assessment values, so that by virtue of the adaptiveness of said evaluation means, the reliability of the evaluation structural variables determined automatically continues to increase as the number of measurements made increases.

In an advantageous configuration of all embodiments as previously described, said device is movable along an essentially equidistant plane relative to the surface and is provided with a distance measurement means which quantitatively logs said relative movement. The given measurement thresholds for structural characteristic values and/or characteristic visual parameters and/or said evaluation structural variables measured across said surface are stored in said memory means.

In a further advantageous embodiment, at least one measuring wheel is provided which alights on the surface during measurement, rotating during the relative moment between the device and the surface to be measured, whereby said at least one measurement wheel can be linked to a rotating angle sensor which emits an electrical signal representative of the rotating angles detected by said measuring wheel.

Furthermore, a memory means can be provided which defines and stores surface visual parameters and coating thickness values continuously or intermittently, respectively spatially periodically, or at predetermined measurement locations on said surface.

This preferred embodiment of the present invention is especially advantageous since the surface to be tested can be, for example, systematically measured over its entire surface.

In said preferred embodiment of the present invention in which a plurality of photo sensors are arranged, the inclusion of a CCD chip is of particular advantage, which in a further preferred embodiment of the present invention is realized as a color CCD chip.

By utilizing a two-dimensional CCD chip, a two-dimensional image of said measurement surface is formed on the CCD chip in the second optical means.

In a preferred embodiment, the measurement surface to be tested is flatly illuminated and mapped on a two-dimensional CCD chip in the second optical means. A variable, respectively a structural variable for the quality of the surface to be tested is then determined by evaluating the (statistical) distribution of the visual characteristics over the measurement surface.

In another preferred embodiment of the present invention, employing a two-dimensional CCD chip while utilizing a spatially narrowly restricted or convergent or focused ray of light on the surface to be tested, allows for the defining of a two-dimensional image of the measurement point on the CCD chip of said second optical means. Various variables of the visual properties of the surface to be tested are then determined by means of (statistical, for example) evaluation of the distribution of brightness on the CCD chip.

In a further preferred embodiment of the device according to the present invention in which the measurement surface to be tested is scanned with a convergent or focussed ray of light, the characteristic visual parameters are determined over the surface to be tested as is the coverage of the individual parameters, as for example, the gloss coverage.

In a further preferred embodiment of one or more of the previously described inventive embodiments of the present device, a histogram of the individual visual parameters is established from the measurement site on the surface to be measured, respectively a table or a histogram is established in which the level of the individual measured visual parameters, for example the gloss, the DOI or the other characteristic parameters is plotted over the frequency. By means of the statistical distribution of the corresponding visual parameters, a variable, structural variable respectively, is determined for the structured surface to be tested.

In a preferred embodiment of the present invention, before beginning a measurement, or before commencing of each individual measurement, a blank image is taken and its values averaged. During measurement, an illuminated image is taken, likewise averaged, and the mean value of said blank image therefrom deducted. A value for the contrast of said image is determined. The brightness of said measured image is standardized using the mean value of said blank image, the illuminated image and the contrast value.

The further evaluation follows using said standardized values, with said standardized image respectively.

In another preferred embodiment of the present invention, said evaluation follows via one or more Fourier transformations. Especially preferred is determining the local frequency variable for each line from a Fourier transformation of said line and the local frequency variable for the entire image being determined from the mean value of the frequency of all lines.

In a further preferred embodiment of the device according to the present invention, said structural parameter is determined through a customary procedure for measurement of surface roughness such as those described in, for example, DIN 4768 (Edition 1990-05), ISO 13565-1 (Edition 1996-12) or in ISO 13565-2 (Edition 1996-12), and which consequently become part of the disclosure.

In a further preferred embodiment, the coating thickness measuring device comprises a switching means for selecting the type of coating thickness sensor suitable for the type of substrate. The type of substrate of said coated surface may thereby be determined automatically by means of a program stored in said memory means, and the switching means may be set such that an appropriate coating thickness sensor is selected for the purpose of determining the coating thickness of said substrate.

The provision of a switching means of this type is particularly advantageous since a particular sensor type is selected for determining the coating thickness by a simple actuation of the switching means; the user may for example be prompted by means of the display to select another sensor type for determining the coating thickness should the coating thickness ascertained with the selected sensor return illogical values.

Exceeding of predetermined limits or values falling below said predetermined limits signifies a departure from the valid measurement range and may be indicated, for example, by the value∞being shown on the display means. The user is thereby prompted to actuate the switching means and to switch to another sensor type. An automatic switching and an automatic selection of an appropriate coating thickness sensor is particularly advantageous when inexperienced users are employing this type of inventive configuration.

It is to be herewith noted that the juxtaposing of the collaborative functioning of individual features according to the present invention is preferable in any optional combination as desired. Particularly preferred are those feature combinations also disclosed through omission of one or more features in the independent and dependent claims. It is deemed obvious to the expert skilled in the art that the present invention would encompass a plurality of further conceivable modifications and realizations above and beyond the embodiments described herewithin. The present invention is hence specifically not restricted only to those forms and examples of embodiments as represented herewithin.

BRIEF DESCRIPTION OF THE SEVERAL VIEWS OF THE DRAWINGS

Further advantages, features and application possibilities of the present invention will now be specified in the following description of embodiments in association with the enclosed drawings, which show.

DETAILED DESCRIPTION OF THE INVENTION

Figure 1:
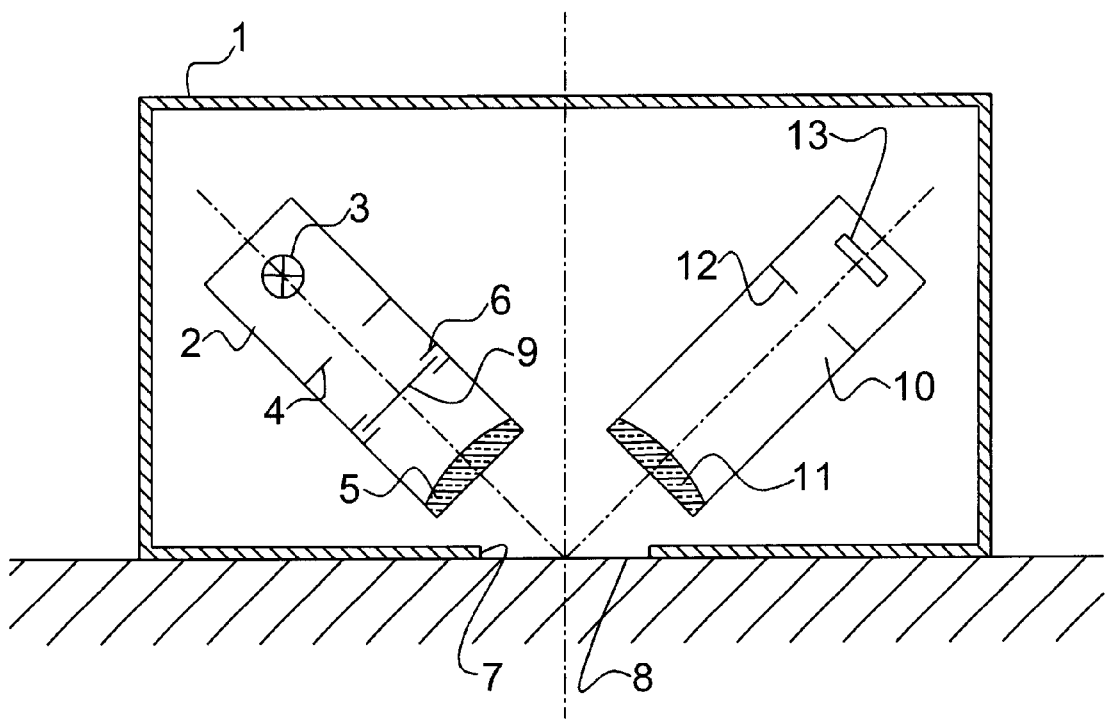
FIG. 1 a section of a first embodiment according to the present invention.

A first embodiment of the present invention will now be described with reference to FIG. 1.

The measurement device for the determination of the quality of structured surfaces represented schematically in this figure, is disposed with a housing in which a first illumination tubus 2 is arranged. A light source 3, a shutter 4, a light pattern device 6 and a lens 5 are provided within said illumination tubus, indicated schematically.

Light emitted from point light source 3 is restricted in its aperture by shutter 4 and impinges onto light pattern device 6. According to given embodiment, a partially transparent light pattern disk 9 can be arranged within the light pattern device 6 by which the phase and/or the amplitude of the light impinging on a portion of the illuminated surface can be influenced in such a manner that the light transmitted exhibits a characteristic light pattern. In this embodiment, the amplitude of the light emitted from light source 3 becomes influenced by the light/dark edges on light pattern disk 9.

The irradiated light is further focused by lens 5, impinging measurement surface 8 through opening 7. The light is reflected off measurement surface 8 and enters measurement tubus 10, which is likewise disposed with a lens 11, a shutter 12 and the actual sensor 13.

The reflection measurement device furthermore comprises a control means (not shown) for controlling the operation of the device, as well as a display means (likewise not shown) which displays the measured structural characteristic values and characteristic visual parameters.

Figure 2:
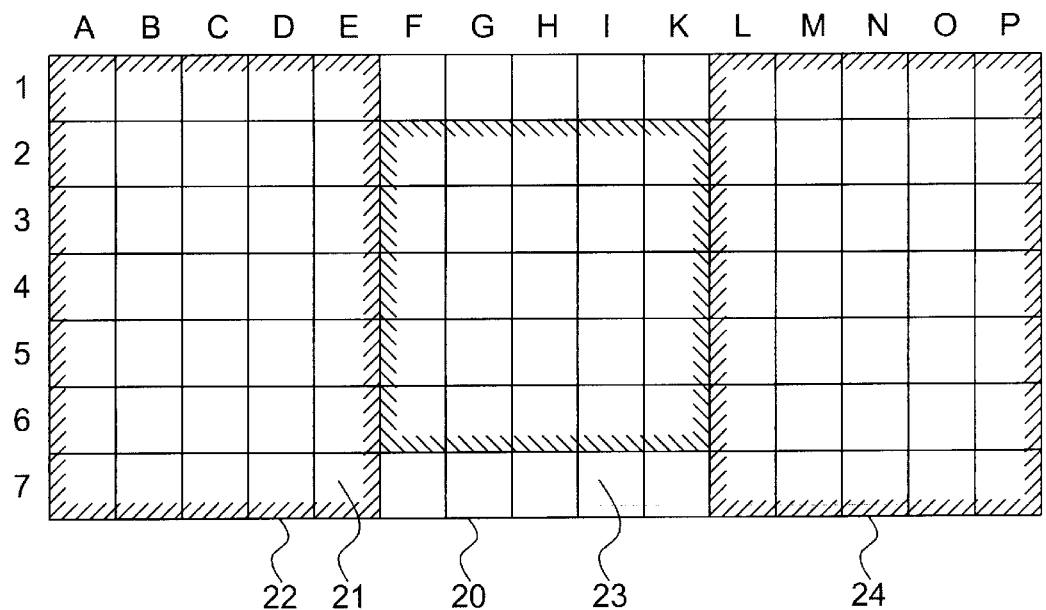
FIG. 2 a further embodiment of a sensor element with which the surfaces used for light measurement can be varied.

The sensor of a further embodiment is represented in FIG. 2. This embodiment is, with the exception of the sensor, configured exactly as that of FIG. 1. FIG. 2 shows sensor device 20 on which a plurality of light-sensitive elements 21 are arranged in rows and columns.

A CCD chip is to be employed in this example, Individual surface elements on the CCD chip surface are linked with photo sensors 22, 23, 24 such that only the signals of said photo sensors 22, 23, 24 are available during measurement.

It should be pointed out that coupling individual surface area elements to photo sensors allows for the realization of the most diverse measurement geometries. Furthermore, not all surface area elements have to undergo measurement.

Figure 3:
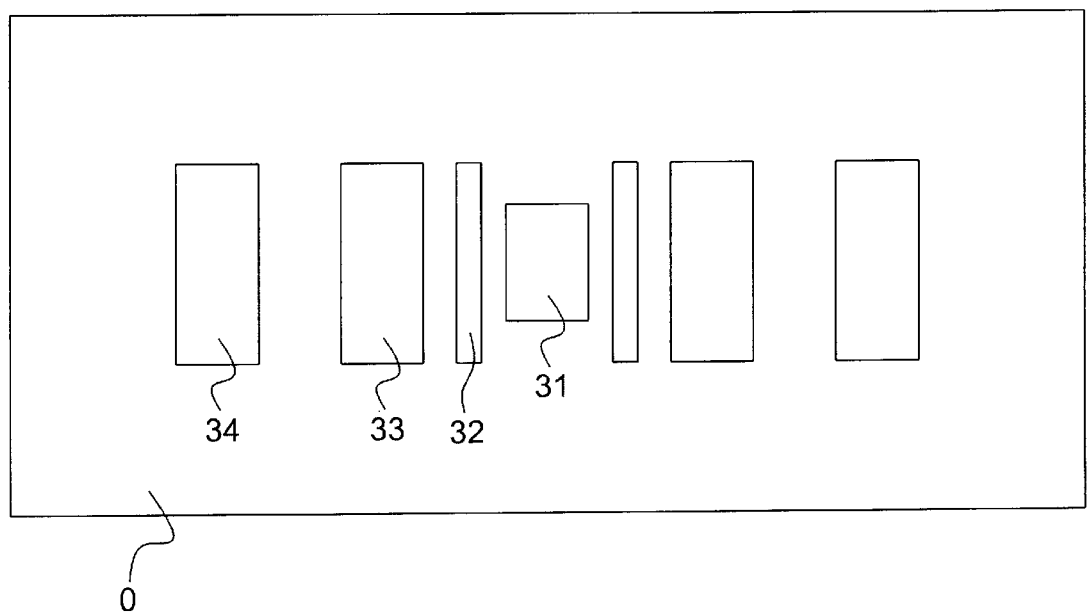
FIG. 3 a further embodiment of a sensor element constituting seven photo sensors with light-sensitive surfaces.

A further embodiment of the sensor device is represented in FIG. 3. The attendant configuration and operation of this device transpires in the same manner as in FIG. 1.

Sensor device 30 is represented in FIG. 3 and is, as in the embodiment in accordance with FIG. 2, realized as a CCD chip.

Individual surface elements on the surface of the CCD chip are linked with photo sensors 31, 32, 33 and 34. Coupling individual surface area elements to photo sensors permits a quick and easy measurement according to various different measurement standards such as, for example, the American ASTM E 430.

In a further embodiment, the basic configuration is exactly as that of the embodiment according to FIG. 1, but no light pattern is projected onto the measurement surface area. A CCD chip is employed as a sensor device, with which all surface elements are measured individually.

Figure 4:
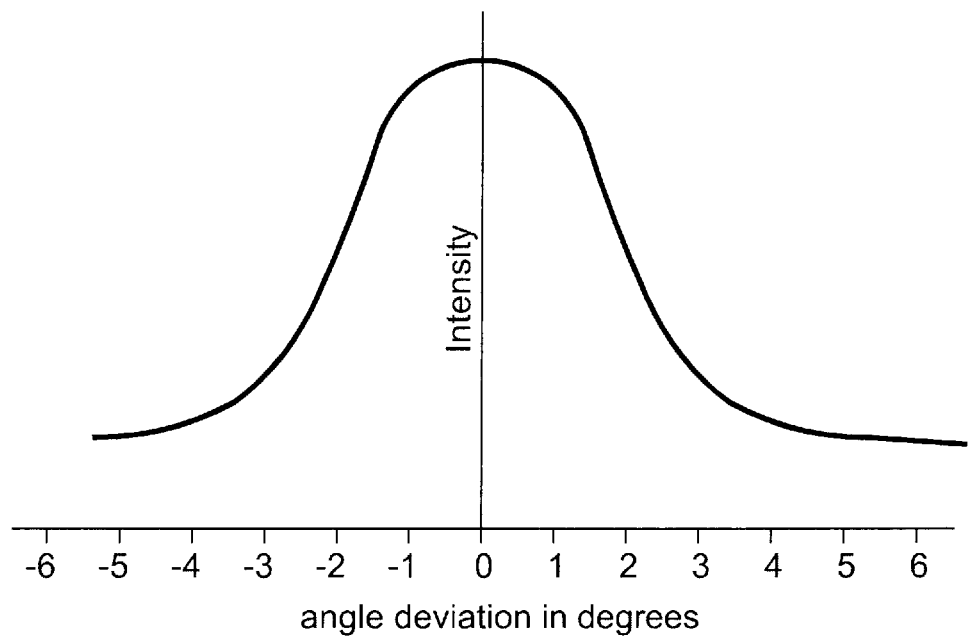
FIG. 4 a diagram showing reflection behavior upon illumination without a light pattern, whereby the measured light intensity is plotted on the ordinate and the angle deviation with respect to the ideal reflection angle is plotted on the abscissa.

In the diagram according to FIG. 4, the measured light intensity is plotted on the ordinate and the angle deviation with respect to the ideal reflection angle is plotted on the abscissa. The measured intensity at its highest is within the range of the ideal reflection angle and then decreases with increasing angle distance. Surface reflection behavior can be assessed in a simple manner from the evaluation of such a plotted curve.

It is furthermore possible to use this curve to derive the parameters which characterize surface reflection behavior according to various standards.

Figure 5:
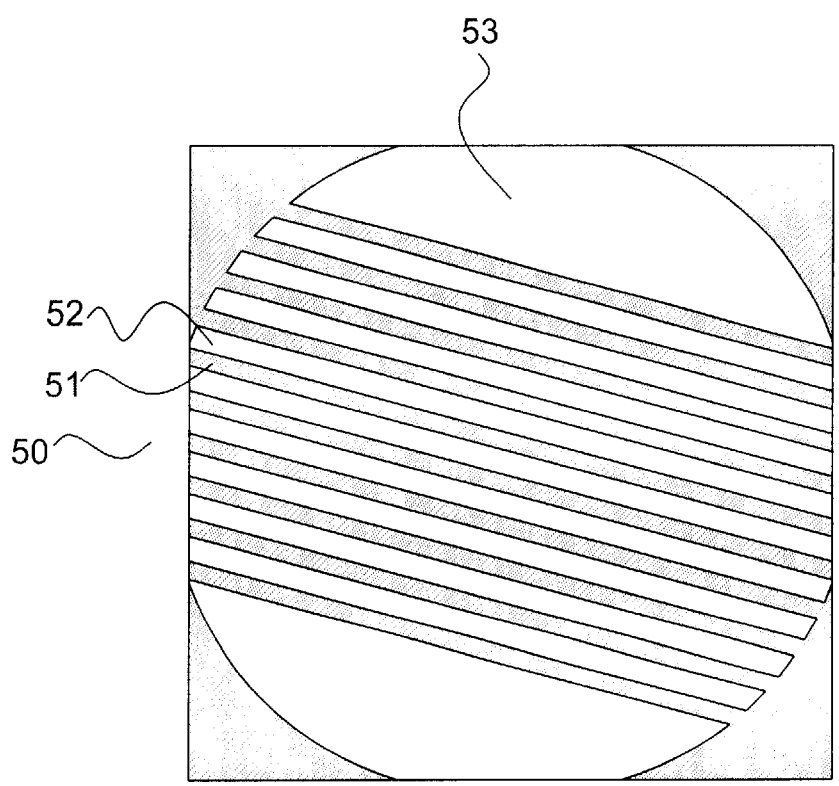
FIG. 5 an image of the light pattern projected onto the measurement surface.

An image reflected from a measurement surface onto the sensor means is represented in FIG. 5. Light pattern 50 exhibits dark edges 51 and light lines 52. A second reflected portion 53 does not exhibit any light pattern.

The contrast within the light pattern decreases with increasing roughness, while a gloss of poorer quality will affect the intensity. Orange peel leads to a distortion of the individual dark and light lines and a structured surface, in the case of a rectangular profile, leads to an offsetting of the individual lines in the recess region. In saw-tooth or triangular profiles, correlating line gradations can be ascertained at the corresponding sections.

Intensity and contrast are evaluated from the image received and the gradients within the light pattern are determined. By forming mean gradient values, a characteristic measurement is determined for the structure of the measurement surface.

Figure 6:
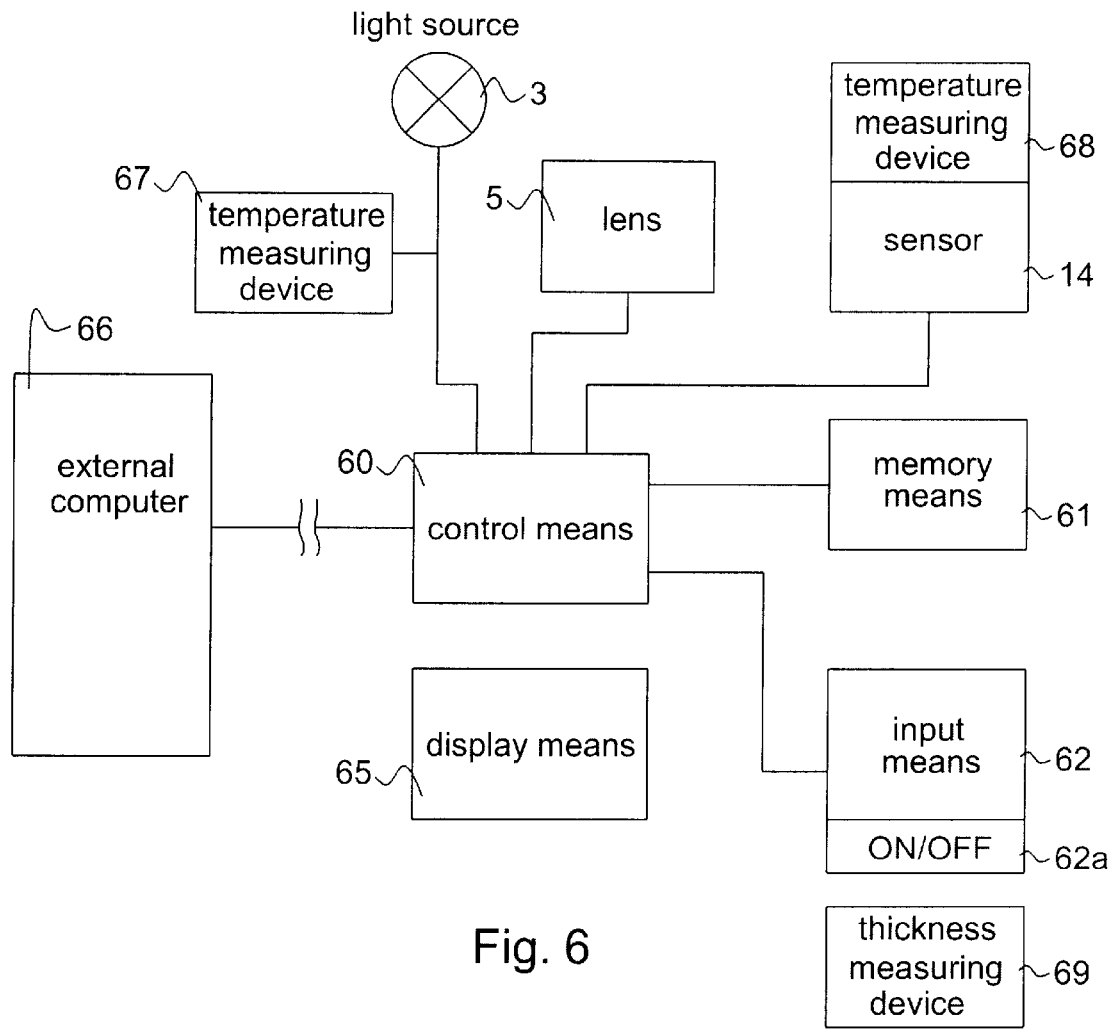
FIG. 6 the basic circuitry configuration of a measurement device as is utilized in the embodiments according to FIGS. 1–5.

FIG. 6 represents the basic divisional circuitry configuration of a measurement device as applied in the embodiments in accordance with FIGS. 1–5.

The basic measurement configuration is the same for all shown embodiments; only its programming will vary according to the type of sensor employed.

The measurement device as a whole is provided with a control means 60 which contains a customary microprocessor controlled by a program which is stored in memory 61. Input means 62 serves for enabling communication between control means 60 and the user and has a number of switches for the purpose of starting the control means' operation and in order to (in the corresponding embodiments) switch between individual modes of operation. Furthermore, the user can enter a type designation for the structured surface to be measured into input means 62, to which subsequent measurements will refer.

In addition to said microprocessor, said control means is provided with input/output means which serve to connect the control means with the individual components of the device.

The control means is linked with light source 3 and sensor 14. The results of a measurement are shown in display 65, which is preferably an LCD display. For further measurement evaluation, a connection to an external computer 66 is provided; the measurement results are also preferably stored in memory means 61.

Power for the measurement device is provided by a battery (not shown).

The measurement device as a whole is preferably accommodated within a housing 1, which has the approximate dimensions of a paperback book.

In the corresponding embodiments, the type of coating thickness sensor may be selected by means of the input means 22.

The electrical output signal of coating thickness sensor 5 is also transmitted to control means 60 for evaluation. Display 65, which is preferably configured as an LCD display, displays the measurement results, To enable further measurement evaluation, a connection to an external computer 66 is provided.

The measuring device is supplied with power by means of a (not shown) battery.

In order to avoid manufacture-contingent deviations of individual measuring devices, each measuring device is preferably calibrated individually. To do so, the measurement device is set upon reference layers such as those provided by standards institutes, and the respective visual characteristics and coating thickness values are measured. The respective values are then stored in memory 61 and are thus permanently available for converting the values assessed by the sensors.

Figure 7:
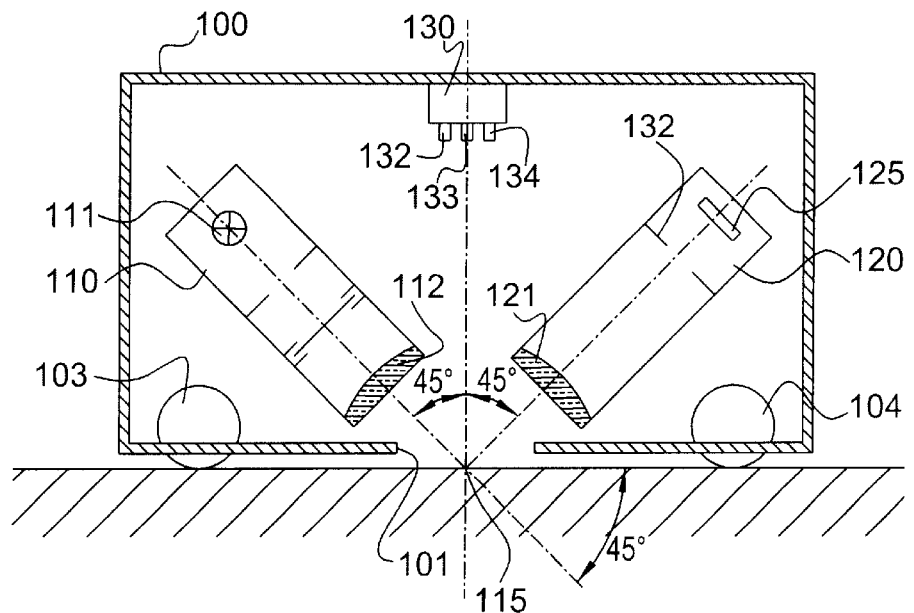
FIG. 7 a further embodiment of the present invention, which is also suitable for other measurements.

A further embodiment of the present invention will now be described with reference to FIG. 7.

In this embodiment, said device is entirely disposed within a housing 100 having an opening 101 for setting the device upon the surface to be measured.

In contrast to the preceding embodiments, the device is however not set directly onto said surface, but rather employs means of (indicated schematically) at least two rubber rolls 103, 104 or at least four rubber wheels 103, 104, which are rotatably supported (not shown) in said housing 100.

At least one of said rubber wheels or rolls is provided with a (not shown) distance measuring means for detecting the angle movements of said rubber wheels 103 and emitting an electrical signal representative thereof.

Said device further comprises a first optical means 110 in which a point light source 111 and a lens 112 are arranged. Said first optical means 110 is such configured that an optical axis is oriented at a predetermined angle (45° in the shown example) relative the surface 115 which is to be measured.

A second optical means is arranged at a second predetermined angle (also 450 here), comprising a lens 121, an aperture 122, and a measurement sensor 123 oriented perpendicular relative said optical axis, which is realized as a color CCD chip in this embodiment.

Three light-emitting elements 132, 133, 134, realized here as LEDs, are arranged on a third optical means 130 which each exhibit different spectral characteristics, e.g. which emit light having different colors.

In the embodiment described here, the light emitted by the LEDs impinges essentially perpendicularly onto the surface to be measured.

The light emitted from the first and third optical means is reflected by said surface 115 which is to be tested and impinges partially on said photo sensor, color CCD chip 125, respectively.

As light-emitting elements 132–134 emit light having different color characteristics in the visible range of the spectrum, it is thereby possible to determine a color parameter for the surface to be measured.

What is claimed is:

1. A device for a quantified determination of the quality of structured surfaces comprising:

a first optical means having at least one light source with light emitting therefrom being directed at a predetermined angle onto a measurement surface which is a portion of a surface to be measured, the measurement surface having at least a first surface section and a second surface section exhibiting a different visual characteristic dependent on the structure of said surface to be measured;

a second optical means arranged at a predetermined angle to said measurement surface for receiving the light reflected from said measurement surface, whereby said second optical means has at least one photo sensor having at least one light-sensitive surface, whereby said at least one photo sensor emits an electrical measurement signal that is characteristic for said reflected light;

evaluation means having at least one processor means and at least one memory means;

an output means;

wherein said first optical means and said second optical means are disposed such that said reflected light is influenced by the structure of said measurement surface;

wherein a characteristic visual parameter of said measurement surface is determinable for said first and second surface sections; and wherein said evaluation means evaluates said reflected light and derives therefrom at least one structural parameter that is representative of at least one structure dependent characteristic of said surface to be measured.

2. The device according to claim 1, wherein said evaluation means evaluates said measurement signal by a program stored in said memory means and stores said measurement signal in said memory means.

3. The device according to claim 1, wherein said second optical means comprises a plurality of photo sensors arranged in rows and columns.

4. The device according to claim 1, wherein at least a first portion of said light emitted from said first optical means exhibits a light pattern.

5. The device according to claim 4, wherein said light pattern irradiated from said first optical means exhibits at least one light/dark edge.

6. The device according to claim 5, wherein the spacing of the pattern lines, light/dark edges respectively, in the reflected light pattern is used to determine the surface curvature.

7. The device according to claim 4, wherein at least a portion of said plurality of light/dark edges is dispersed at least sectionally parallel to one another.

8. The device according to claim 4, wherein said light pattern irradiated from said first optical means exhibits a plurality of light/dark edges, and wherein at least a portion of said plurality of light/dark edges is arranged in a form taken from a group of forms consisting of a grid, a lattice and a circular form.

9. The device according to claim 4, wherein said first portion of said light emitted from said first optical means exhibits said light pattern and that a second portion thereof is directed without light pattern onto said measurement surface.

10. The device according to claim 4, wherein at least one of said at least one visual parameter is determined from said measurement signals of said photo sensors which receive said second portion of said light emitted from said first optical means as reflected from said measurement surface.

11. The device according to claim 1, wherein said evaluation means determines a gradation of said measurement signal for at least a portion of said plurality of photo sensors from the difference defined between measurement signals of an adjacent pair of said photo sensors.

12. The device according to claim 11, wherein said evaluation means determines said gradation of said measurement signal for at least a portion of said plurality of photo sensors from the difference defined between measurement signals of said portion of said plurality of photo sensors and a measurement signal of all of the remainder of said plurality of photo sensors.

13. The device according to claim 11, wherein said evaluation means determines at least one average of at least a portion of said gradation and determines therefrom said characteristic structural parameter for said at least one structure dependent characteristic of said measurement surface.

14. The device according to claim 1, wherein at least two characteristic visual parameters are determined for at least one surface section of said first and second surface sections of said measurement surface.

15. The device according to claim 14, wherein at least one temperature measuring device is arranged in as close proximity as possible to at least one of said plurality of photo sensors for determining the characteristic temperature of the respective photo sensors so that a temperature-corrected determination of said at least one structural characteristic value is obtainable.

16. The device according to claim 14, wherein said visual parameters measured across said measurement surface are stored in said memory means.

17. The device according to claim 14, wherein at least one characteristic visual parameter is determined for each of a plurality of points on said measurement surface.

18. The device according to claim 14, wherein at least one threshold value is definable for said at least one structural parameter.

19. The device according to claim 18, wherein said threshold value is a lower threshold value, and wherein upon said defined threshold being undercut, an alarm signal is issued.

20. The device according to claim 18, wherein said threshold value is an upper threshold value, and wherein upon said defined threshold being exceeded, an alarm signal is issued.

21. The device according to claim 14, wherein at least one threshold value is definable for said at least one characteristic optical parameter.

22. The device according to claim 21, wherein said threshold value is a lower threshold value, and wherein upon said defined threshold being undercut, an alarm signal is issued.

23. The device according to claim 22, wherein said threshold value is an upper threshold value, and wherein upon said defined threshold being exceeded, an alarm signal is issued.

24. The device according to claim 21, wherein at least one of said at least one threshold value is automatically determined through measurement of at least one reference surface.

25. The device according to claim 14, wherein one of said at least one characteristic visual parameter is taken from a group of visual parameters comprising the gloss, the haze, the distinction of image (DOI), the ripple (orange peel), and the color of the surface.

26. The device according to claim 14, further comprising a coating thickness measuring device for determining the layer thickness of the coating applied to said surface to be measured, said coating thickness measuring device having at least one coating thickness sensor that generates an electric coating thickness output signal that is representative of the coating thickness to be determined;

wherein said control means determines a coating thickness value by evaluating said coating thickness output signal, and determines at least one visual parameter characteristic of said measurement surface by evaluating the light received by said at least one photo sensor as reflected by said measurement surface; and wherein said output means displays said at least one coating thickness value and said at least one visual parameter.

27. The device according to claim 26, wherein said coating thickness measuring device comprises at least one sensor of the group of sensors consisting of a permanent magnet, a magnetic flux density sensor means, a Hall effect sensor means, and an eddy current measuring coil.

28. The device according to claim 26, wherein said coating thickness measuring device comprises an ultrasonic transmitter and ultrasonic receiver means for determining said coating thickness.

29. The device according to claim 26, wherein said coating thickness measuring device comprises a heat generating, a sound generating and an acoustic sensor means for determining said coating thickness.

30. The device according to claim 26, wherein said coating thickness measuring device has at least two different sensor means for determining the coating thickness of said measurement surface, whereby at least one first coating thickness sensor is provided for determining the layer thickness on magnetic substrates, and whereby at least one second coating thickness sensor is provided for determining the layer thickness on non-magnetic substrates.

31. The device according to claim 26, wherein said coating thickness measuring device has at least two different sensor means for determining the coating thickness of said measurement surface, whereby at least one first coating thickness sensor is provided for determining the layer thickness on electrically conductive substrates, and whereby at least one second coating thickness sensor is provided for determining the layer thickness on electrically non-conductive substrates.

32. The device according to claim 26, further comprising means for switching the coating thickness sensors for determining the layer thickness on magnetic, non-magnetic and plastic substrates.

33. The device according to claim 14, wherein the light pattern reflected from said surface to be measured and received by said measuring means is used to determine a surface curvature.

34. The device according to claim 14, wherein said surface to be measured has a sharpness of depth to said image, and wherein said sharpness is adjustable on said measuring means such that said measurement values is essentially not influenced by a curvature of said surface to be measured.

35. The device according to claim 14, wherein said surface to be measured has a sharpness of depth to said image, and wherein said sharpness is adjustable on said measuring means such that said at least one characteristic visual parameter is essentially not influenced by a curvature of said surface to be measured.

36. The device according to claim 1, wherein said characteristic visual parameters comprise the gloss or the haze or the distinction of image (DOI) of said measurement surface.

37. The device according to claim 1, wherein said characteristic visual parameters are a representative measure of typical wavelength and amplitude (orange peel) of said measurement surface coating thickness topology at a predetermined wavelength interval, whereby said evaluation ensues at least one range of wavelength.

38. The device according to claim 1, wherein said predetermined angle at which light emitted from said first optical means is directed onto said measurement surface and said predetermined angle at which said second optical means receives said light reflected from said measurement surface is variably adjustable and encompass angles of 0°, 5°, 10°, 15°, 20°, 30°, 45°, 60°, 75°, 80°, and 85°.

39. The device according to claim 1, further comprising a third optical means having at least one light source and emitting light with a predetermined spectral characteristic that is directed at a predetermined angle onto said measurement surface.

40. The device according to claim 39, wherein said predetermined angle at which light emitted from said third optical means is directed onto said measurement surface is variably adjustable and encompass angles of 0°, 5°, 10°, 15°, 20°, 30°, 45°, 60°, 75°, 80°, and 85° in particular.

41. The device according to claim 39, wherein said light emitted from said third optical means is directed at such an angle onto the surface that the directed light directly reflected from said measurement surface in accordance with the Fresnel reflection has a different angle with respect to said measurement surface than the angle between said measurement surface and said directed surface reflected light that is emitted from said first optical means.

42. The device according to claim 39, wherein said at least one light source of said third optical means comprises at least two light-emitting elements with each light emitted having a different spectral characteristic so that a varied range of emitted wavelengths result.

43. The device according to claim 42, wherein said emitted wavelength-ranges of said light-emitting elements at least partially overlap in the range of the visible light spectrum and that the emitted spectral characteristics of said light-emitting elements are linearly independent of one another.

44. The device according to claim 39, wherein said at least one light source of said first optical means and said third optical means is provided with at least one light source taken from a group of light sources comprising light-emitting diodes and laser light sources.

45. The device according to claim 39, wherein said third optical means emits essentially divergent light.

46. The device according to claim 39, wherein said third optical means emits essentially convergent light.

47. The device according to claim 39, wherein at least one temperature measuring device is arranged in as close proximity as possible to at least one of said at least one light source of said first optical means and to at least one light source of said third optical means for determining the characteristic temperature of the respective light source so that a temperature corrected determination of said at least one structural characteristic value is obtainable.

48. The device according to claim 39, wherein said measurement surface is scannable by said light emitted by at least one of said first and said third optical means.

49. The device according to claim 39, wherein said first and third optical means emits essentially directional light.

50. The device according to claim 1, wherein at least one of said plurality of photo sensors is disposed with at least three photo-sensitive elements having electrical outgoing signals that can be individually determined and differ with respect to their spectral characteristics so that the ascertained color of the reflected light will serve as a visual parameter of said measurement surface.

51. The device according to claim 1, wherein said first optical means emits essentially parallel light.

52. The device according to claim 1, wherein said first optical means emits at least one point of light with a predetermined diameter perpendicular to the direction of propagation.

53. The device according to claim 1, wherein at least one of said at least one visual parameter is determined from said measurement signals of said photo sensors which receive said second portion of said light emitted from said first optical means as reflected from said measurement surface.

54. The device according to claim 1, wherein at least a portion of a mapped path of said at least one light/dark edge on said plurality of photo sensors is determined and a characteristic profile height parameter of said measurement surface is determined from a course deviation of the measured path from the ideal path.

55. The device according to claim 1, wherein said structural parameter is determined by a triangulation procedure.

56. The device according to claim 1, wherein at least one of said at least plurality of photo sensors determines the intensity of said light emitted from said first optical means and reflected by said surface to be measured and that said evaluation means saves in said memory means a characteristic location parameter for the location to be measured, and that said measured intensity evaluation value determines a characteristic distance parameter for a distance from the device to said surface to be measured and saves same in said memory means.

57. The device according to claim 1, wherein said first optical means is provided with a scanning device for scanning said surface to be measured.

58. The device according to claim 1, wherein said evaluation means determines at least one of said at least one structural parameter from said distance parameters and said characteristic location parameters.

59. The device according to claim 1, wherein said evaluation means determines at least one quantitative slope gradient parameter for the gradient characteristic of the structure of said surface to be tested.

60. The device-according to claim 1, wherein said evaluation means determines at least one quantitative sharpness parameter for the definition of sharpness of edges of the structure of said surface to be measured.

61. The device according to claim 1, wherein at least one evaluation structural parameter is derived from said at least one structural parameter and at least one of the cited characteristic visual properties (gloss, haze, DOI, orange peel) or that at least one evaluation structural parameter is determined for each of the determined characteristic visual parameters (gloss, haze, DOI, orange peel).

62. The device according to claim 1, further comprising an input means for entering by the user a type designation for said surface to be measured and that subsequent measurements with reference to this type designation are stored long-term in said memory means.

63. The device according to claim 62, wherein the user switches said evaluation means to a type change mode by activating a type change switch and that upon entering another type designation, the results from subsequent measurements with reference to this other type designation are stored long-term in said memory means.

64. The device according to claim 62, wherein subsequent to each measurement, the user can enter his own evaluations of each surface measured by input of a user-defined assessment value in said input means and that said user-defined assessment value together with at least one of said measurement parameters and characteristic values and said at least one evaluation structural parameter is stored long-term in said memory means, whereby said user-defined assessment value is a subjective measure of the quality of said measurement surface as defined by the user, and wherein the range of said user-defined assessment values encompasses at least two differing values corresponding to "good" and "poor."

65. The device according to claim 64, wherein said evaluation means utilizes at least a portion of said user-defined assessment values and corresponding measurement parameters and characteristic values as filed in said memory means for the automatic determination of at least one of said at least one threshold value for said type designation.

66. The device according to claim 1, further comprising an ON/OFF switch that upon switching on the device, a signal prompts the user to enter a type designation into said input means for the designation of type of said surface to be measured.

67. The device according to claim 1, wherein the device is movable along an essentially equidistant plane relative the measurement surface and has a distance measurement means that quantitatively logs said relative movement, and further comprising a memory means in which the measured structural characteristic values measured across said measurement surface are stored.

68. The device according to claim 67, wherein said visual parameters measured across said measurement surface are stored in said memory means.

69. The device according to claim 67, further comprising at least one measuring wheel that alights on the surface during measurement and rotates during the relative moment between the device and said surface to be measured.

70. The device according to claim 69, wherein at least one of said at least one measurement wheels is linked to a rotating angle sensor that emits an electrical signal representative of the rotating angles detected from said measuring wheel.

71. The device according to claim 1, wherein said first optical means emits convergent light on said measurement surface.

72. The device according to claim 71, wherein said at least one characteristic visual parameter is one of a plurality of characteristic visual parameters, and wherein each of said plurality of characteristic visual parameters is evaluable according to predetermined parameter ranges.

73. The device according to claim 72, wherein each of said plurality of characteristic visual parameters within a predetermined number of predetermined parameter ranges is evaluable according to statistical rules.

74. The device according to claim 1, wherein light emitted from at least one of said first, second and third optical means and reflected by said surface to be measured is essentially focused onto an aperture or block aperture.

75. The device according to claim 74, wherein said aperture or block aperture has essentially a circular surface perpendicular to said reflected light direction of propagation.

76. The device according to claim 1, wherein said at least one of said plurality of photo sensors is illuminated according to a method selected from a group of methods consisting of light-field, dark-field, striae, and phase.

77. The device according to claim 1, wherein said surface to be measured has a curvature that is determined and utilized for a correction of the measurement values so that said at least one characteristic visual parameter is at most only negligibly influenced by said curvature.

78. A method for a quantified determination of the quality of structured surfaces with the application of a device, said method comprising:
  directing light with a first optical means having a first light source at a predetermined angle onto a measurement surface to be measured, wherein said measurement surface has at least a first surface section and a second surface section exhibiting a different visual characteristic dependent on the structure of said measurement surface;
  receiving light reflected from said measurement surface with a second optical means having at least one photo sensor that is oriented at a second predetermined angle to said measurement surface, whereby said at least one photo sensor emits an electrical measurement signal that is characteristic for said received light,
  controlling with an evaluation means a measuring process sequence with at least one processor means and storing said electrical measurement signal in a memory means,
  issuing with an output means a measurement result,
  wherein for each of said at least two surface sections a characteristic visual parameter of said measurement surface is determined; and
  evaluating with said evaluation means said reflected light and deriving therefrom at least one structural parameter that characterizes the structure dependent characteristic of the surface.

* * * * *